US010249669B1

(12) United States Patent
Fine et al.

(10) Patent No.: US 10,249,669 B1
(45) Date of Patent: Apr. 2, 2019

(54) IMAGE SENSORS HAVING TWO OR MORE LIGHT SENSITIVE SUBAREAS FOR RECEIVING TWO OR MORE IMAGES OF A SAMPLE FROM A COMPONENT

(71) Applicant: Alentic Microscience Inc., Halifax (CA)

(72) Inventors: Alan Marc Fine, Prospect (CA); Madhuranga Srinath Rankaduwa, Halifax (CA)

(73) Assignee: Alentic Microscience Inc., Halifax, Nova Scotia (CA)

( * ) Notice: Subject to any disclaimer, the term of this patent is extended or adjusted under 35 U.S.C. 154(b) by 0 days.

(21) Appl. No.: 16/210,098

(22) Filed: Dec. 5, 2018

Related U.S. Application Data

(62) Division of application No. 15/963,894, filed on Apr. 26, 2018, now Pat. No. 10,153,317.

(51) Int. Cl.
*G01N 33/49* (2006.01)
*H01L 27/146* (2006.01)
*G01N 21/27* (2006.01)

(52) U.S. Cl.
CPC ....... *H01L 27/14632* (2013.01); *G01N 21/27* (2013.01); *G01N 33/49* (2013.01); *H01L 27/14636* (2013.01); *H01L 27/14687* (2013.01)

(58) Field of Classification Search
CPC .............................. G01N 21/27; G01N 33/49
USPC ................................................ 250/208.1, 239
See application file for complete search history.

(56) References Cited

U.S. PATENT DOCUMENTS

| 9,569,664 B2 * | 2/2017 | Judkewitz .......... G06K 9/00624 |
| 2004/0140417 A1 | 7/2004 | Karin |

OTHER PUBLICATIONS

Pyxalis, "Semi-custom platforms and method from niche markets to consumer applications", Minalogic Meetings, Grenoble, 2017 (40 pages).
USPTO transaction history, application as filed and pending claims for U.S. Appl. No. 15/963,894.

\* cited by examiner

*Primary Examiner* — Que Tan Le
(74) *Attorney, Agent, or Firm* — Fish & Richardson P.C.

(57) ABSTRACT

Among other things, an integral image sensor includes a sensor surface having a surface area at which light-sensitive pixels are arranged in rows and columns. The surface area includes two or more light-sensitive subareas each of the subareas having been configured to have been diced from a wafer along two orthogonal dimensions to form a discrete image sensor. The two or more light-sensitive subareas are arranged along one of the two orthogonal dimensions. The sensor surface of the integral image sensor is flat and continuous across the two or more subareas.

18 Claims, 4 Drawing Sheets

IMAGE SENSORS HAVING TWO OR MORE LIGHT SENSITIVE SUBAREAS FOR RECEIVING TWO OR MORE IMAGES OF A SAMPLE FROM A COMPONENT

CROSS-REFERENCE TO RELATED APPLICATIONS

This application is a divisional application of and claims priority to U.S. application Ser. No. 15/963,894, filed on Apr. 26, 2018.

BACKGROUND

This description relates to image sensors.

Individual discrete image sensors used in digital camera applications, for example, are typically obtained from a wafer on which the sensors, formed in rows and columns, are separated by dicing the wafer. In some dicing processes, slices are made in two orthogonal directions across the wafer to form saw streets between the rows and columns of sensors. Each image sensor has an array of light-sensitive pixels usually arranged in rows and columns parallel to the rows and columns along which the sensors themselves are arranged. When the sensors are formed on the wafer, subareas that do not contain light-sensitive pixels are formed between the sensors to provide space for the dicing slice or kerf to be made without damaging the sensors. To incorporate a sensor into a circuit electrical connections are made from the circuit to interconnection contacts that are typically arranged along two or more sides of the sensor.

Image sensors are sometimes used in applications that do not include lenses between the object and the sensor, for example, in contact imaging systems such as the ones described in U.S. patent application Ser. No. 14/173,500, filed Feb. 5, 2014, and incorporated here by reference.

SUMMARY

In general, in an aspect, an integral image sensor includes a sensor surface having a surface area at which light-sensitive pixels are arranged in rows and columns. The surface area includes two or more light-sensitive subareas each of the subareas having been configured to have been diced from a wafer along two orthogonal dimensions to form a discrete image sensor. The two or more light-sensitive subareas are arranged along one of the two orthogonal dimensions. The sensor surface of the integral image sensor is flat and continuous across the two or more subareas. Implementations may include one or a combination of two or more of the following features. The two orthogonal dimensions along which the wafer would have been diced are parallel to the directions of the rows and columns of the pixels. A single row or column of the subareas is arranged along one of the two orthogonal dimensions. There are interconnects along sides of the image sensor for making electrical contact to the light-sensitive subareas. There are interconnects along a side or sides of a row or column that span two or more of the subareas for making electrical contact to the light-sensitive subareas. There are interconnects along not more than the two opposite sides of a row or column that spans two or more of the subareas for making electrical contact to the light-sensitive subareas. The surface area includes at least one non-light-sensitive subarea between two of the light-sensitive subareas. The non-light-sensitive subarea was configured to have become a saw street had the wafer been diced. A sensor drive circuit is coupled to the integral image sensor. A memory is coupled to the sensor drive circuit. A processor and an application are coupled to the memory. A chamber is associated with the sensor surface. The chamber comprises a surface spaced from the sensor surface by a predetermined distance associated with a monolayer of a specimen.

In general, in an aspect, an integral image sensor includes a sensor surface having a surface area in which light-sensitive pixels are arranged in rows and columns. The surface area includes two or more light-sensitive subareas in a row or column. Successive light-sensitive subareas along the row or column are separated by non-light sensitive areas. The sensor surface of the integral image sensor is flat and continuous across the two or more subareas.

Implementations may include one or a combination of two or more of the following features. There are interconnects along sides of the image sensor. There are interconnects along a side or sides of a row or column that span two or more subareas, for making electrical contact to the light-sensitive subareas. There are interconnects along not more than the two opposite sides of a row or column that spans two or more of the subareas for making electrical contact to the light-sensitive subareas. The non-light-sensitive subarea between the light-sensitive subareas was configured to have become a saw street had the wafer been diced. A sensor drive circuit is coupled to the integral image sensor. A memory is coupled to the sensor drive circuit. A processor and an application are coupled to the memory. A chamber is associated with the sensor surface. The chamber includes a surface spaced from the sensor surface by a predetermined distance associated with a monolayer of a specimen.

In general, in an aspect, a large-area high-aspect-ratio integral image sensor includes two or more light-sensitive subareas in a row at a sensor surface. There are successive light-sensitive subareas along the row and they are separated by non-light sensitive areas. There is a chamber configured to confine a monolayer of blood or other sample at the sensor surface.

Implementations may include one or a combination of two or more of the following features. The sensor surface of the integral image sensor is flat and continuous across the two or more light-sensitive subareas. There are interconnects along sides of the image sensor for making electrical contact to the light-sensitive subareas. There are interconnects along a side or sides of a row or column that span two or more of the subareas for making electrical contact to the light-sensitive subareas. There are interconnects along not more than the two opposite sides of a row or column that spans two or more of the subareas for making electrical contact to the light-sensitive areas. A sensor drive circuit is coupled to the integral image sensor. A memory is coupled to the sensor drive circuit. A processor and an application are coupled to the memory. An application is configured to perform a blood count or other analysis of the specimen. A chamber is associated with the sensor surface. The chamber comprises a surface spaced from the sensor surface by a predetermined distance associated with a monolayer of a specimen.

In general, in an aspect, a wafer bearing rows of image sensors is sliced to separate the rows from one another. Each of the rows is sliced to form one or more large-area high-aspect-ratio sensors each comprising two or more of the image sensors in a single row. The large-area sensors are not sliced into single image sensors.

In general, in an aspect, image information is received from a large-area high-aspect-ratio integral image sensor.

The image information is representative of a monolayer of a blood or other specimen. A blood count or other analysis is performed on the specimen using the received image information.

In general, in an aspect, at least one component is configured to provide two or more images of a sample, and a large-area high-aspect-ratio integral image sensor has two or more light-sensitive subareas positioned to receive the two or more images from the component.

Implementations may include one or a combination of two or more of the following features. The component includes a beam-splitting component configured to split a collimated image of the sample into two or more copies of the collimated image, and the two or more light-sensitive subareas are positioned to receive the two or more copies of the collimated image from the beam splitting apparatus. An optical path from the beam splitting component to the large-area high-aspect-ratio integral image sensor is free of any intervening color filter array on the image sensor. The component is configured to acquire the two or more images of the sample from two or more different perspectives, and the two or more light-sensitive subareas are positioned to receive the two or more images of the sample.

In general, in an aspect, a component is configured to provide two or more images of a sample, and a large-area high-aspect-ratio integral image sensor has two or more light-sensitive subareas positioned to receive the two or more images from the component.

Implementations may include one or a combination of two or more of the following features. The component includes a beam-splitting component and optics to project two or more identical images of the sample on to two or more light-sensitive subareas. There is an optical path from the beam splitting component to the large-area high-aspect-ratio integral image sensor. The component is configured to acquire the two or more images of the sample from two or more layers of the sample that lie at different distances from the apparatus and to focus the images on two or more light-sensitive subareas.

These and other aspects, features, and implementations can be expressed as methods, apparatus, systems, components, program products, methods of doing business, means or steps for performing a function, and in other ways.

These and other aspects, features, and implementations will become apparent from the following descriptions, including the claims.

DESCRIPTION

Figure 1:
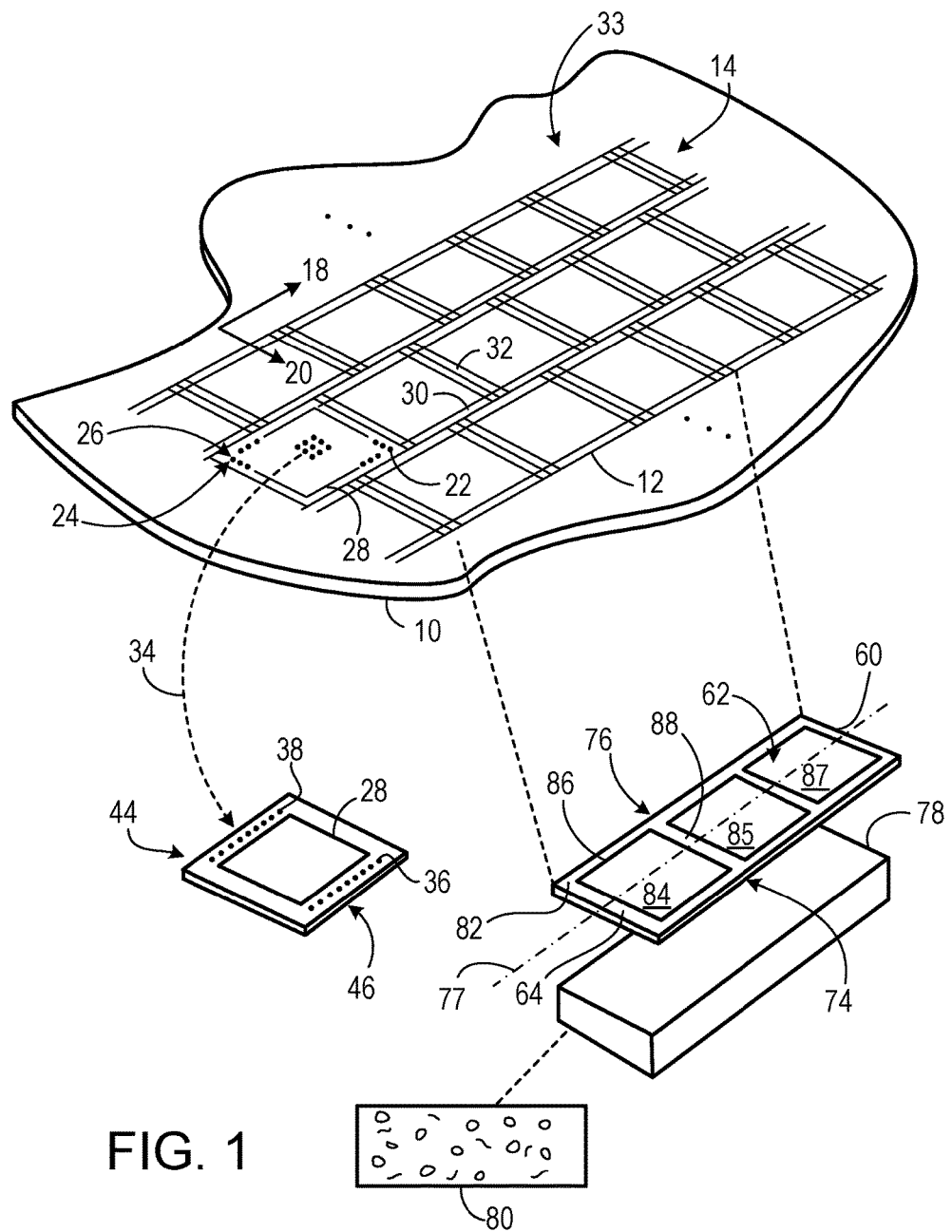
FIG. 1 is a schematic top view of a portion of a wafer.

As shown in FIG. 1, during fabrication, image sensors 12 are arranged in rows 14 along one dimension 18 across a semiconductor wafer 10, and the rows are arranged side-by-side along a second dimension 20 orthogonal to dimension 18. In some cases, the rows are arranged so that the image sensors in adjacent rows are staggered as shown in FIG. 1. In some cases, the rows can be arranged so that the sensors in adjacent rows are aligned in columns.

Each image sensor has an array of light-sensitive pixels 22 also arranged in a pattern, e.g., a pattern of rows and columns 24, 26, along the dimensions 18, 20 within a light-sensitive subarea 28 of the image sensor. Non-light-sensitive subareas 30, 32 extend throughout the wafer along the dimensions 18, 20 between adjacent light-sensitive subareas 28. All of the image sensors and their pixels are exposed at a single continuous smooth flat surface 33 of the wafer. In typical wafer processing, to dice the wafer into individual discrete sensors 34, a variety of processes, such as slicing, laser cutting, or etching, can be used to remove strips of material in the non-light-sensitive subareas leaving saw streets between the image sensors.

To enable each of such discrete sensors to be connected to a sensor drive circuit that can drive the sensor and receive its image signals, interconnection contacts are formed in the wafer along opposite edges 36, 38 of the image sensors that lie in each of the rows 14. When the wafer is diced, the interconnection contacts typically are accessible from the top surface adjacent to the light-sensitive subarea 28 along the two opposite sides 44, 46 of each discrete sensor.

In some cases, in which the wafer is diced to yield discrete image sensors, the resulting sensors could be used, for example, in digital camera applications or in microscopy.

In applications of such image sensors in lensless (e.g., contact) microscopic imaging, for example blood counting applications and many others, it can be desirable to have both a high density (resolution) of pixels in the light-sensitive subareas and a large light-sensitive area. Image sensors typically available commercially at relatively low cost may have high pixel counts (say 10-20 megapixels in a full-frame camera-type sensor). The surface areas of such image sensors are typically constrained by factors such as the optical features of the lenses (e.g., focal length) and cameras (e.g., aspect ratios of the intended final images) in which they will be used. The image sensors are usually rectangular and have a relatively low-aspect-ratio, say 2:1 or 3:2. Some full frame camera sensors for example are 24 mm×36 mm. Larger area sensors of various shapes and aspect ratios may be available but at high cost based on limited production, difficulty of manufacture, the need for custom design or other considerations.

Inexpensive, readily available larger area sensors would be useful and usable in near-field imaging applications. In theory one might form a large-area sensor for near field imaging applications by mounting commercially available small aspect ratio sensors as tiles in a row or in rows and columns. For many such applications, however, it can be important for the entire large-area of the image sensor to have a smooth continuous flat (i.e., coplanar) surface. Achieving such a surface using tiled single discrete sensors can be difficult and, if possible at all, expensive.

A large-area high-resolution high-aspect-ratio image sensor 60 having a continuous smooth flat surface 62 can be made at a relatively low cost from an existing wafer 10 on which individual low-aspect-ratio image sensors (such as digital camera sensors) 12 have been formed and are ready for dicing as explained below. The techniques that we describe are particularly useful if all interconnects for each individual low-aspect-ratio image sensor on the wafer are arranged along not more than two opposite sides of the sensor, and if all individual sensors in a row have their interconnects aligned similarly on the wafer.

To form the high-aspect-ratio sensor, instead of dicing in both of the orthogonal directions 18, 20 to form single discrete image sensors, first the wafer is sliced only in the dimension 18 along which the interconnects are oriented, to form strips of image sensors in single rows. Each of the rows is then sliced in the orthogonal dimension 20 to form large-area high-resolution high-aspect-ratio image sensors 60 each having a desired number, say two, three, four, five, six, or more (including possibly a very large number) of sensors 64 in a row.

We use the term "large-area" broadly to include, for example, areas larger than the light-sensitive areas of typical digital camera image sensors, for example, areas larger than 10 square millimeters, ½ square centimeter, 1 square centimeter, 2 square centimeters, 5 square centimeters or more.

We use the term "high-aspect-ratio" to refer, for example, to an aspect ratio larger than 2:1, for example, 3:1, 4:1, 6:1, 8:1 or larger.

We use the term "low-aspect-ratio" to refer, for example, to an aspect ratio no larger than 2:1 or in the range between 1:1 and 2:1.

We use the term "high resolution" to mean, for example, a pixel spacing smaller than 5 microns, or 3 µm, or 1 µm, or sub-micron.

Each of the large-area image sensors 60 has interconnection contacts along the two opposite sides 74, 76 parallel to an axis 77 passing through the centers of the discrete sensors along the strip, for connection to a sensor drive circuit 78 that can drive and receive signals from all of the pixels of all of the discrete light sensitive subareas of the large-area image sensor. Controlling and reading signals from the multiple light sensitive subareas is possible using available digital camera controllers that can perform similar functions for multiple digital cameras simultaneously. Together those pixels (which can have a high resolution spacing) represent and can be processed to generate a large-area image 80 which can in turn be viewed, processed, or analyzed, for example, in a blood count application.

The surface of such a large-area image sensor is as continuous, smooth, and flat as the wafer from which it is cut. The large-area high-resolution high-aspect-ratio image sensor 60 has a large surface area 82 that includes light-sensitive sub-areas 84, 85, 87 associated with the respective image sensors 86 in the row separated by non-light-sensitive areas 88.

The large-area high-resolution high-aspect-ratio image sensor 60 also has a high-aspect-ratio (of its width to its length) that may be many times the aspect ratio of the single discrete image sensors that might be diced from the original wafer. In theory it would be possible to dice large-area normal aspect ratio sensors from a wafer in which each of the diced sensors would have, say, three image sensors in a row in one dimension and three columns of the image sensors in the other direction. However, such image sensors would not be practically useful because the interconnection contacts for the edges of the sensors that were embedded within the rows and columns of the sensor would be difficult or impossible to access.

A large-area high-resolution high-aspect-ratio image sensor 60 having a high-aspect-ratio and some non-light-sensitive subareas might not be useful for ordinary digital cameras or some other imaging applications designed to generate images formed by a camera lens. But for some applications, e.g., lensless microscopic imaging for blood counting and many others, an image sensor having a high-aspect-ratio could be useful even with non-light-sensitive subareas, if it thereby achieves a large image area, in turn providing a larger field of view. In some blood counting applications, the goal is accurately to identify and count various types of constituents in a precise tiny volume of blood that is representative of blood of a person from whom a specimen was drawn. A larger field of view results in a larger sample size, and consequently in more accurate counts, and can be useful in a wide variety of other applications. The aspect ratio of the sensor or the existence of non-light-sensitive subareas is not an impediment to this counting as long as (a) the volume of blood that is imaged by the light-sensitive subareas is known and (b) the distribution of constituents in the volume of blood that is imaged by the light-sensitive subareas is representative of the overall distribution of constituents in the specimen. For most constituents a correct result can be achieved by assuring that the constituents have not been uncharacteristically concentrated in certain places within the sample, such as at the locations of the non-light-sensitive subareas. Approaches for assuring the uniform distribution of constituents are described in, for example, U.S. patent application Ser. No. 15/482,215, filed on Apr. 7, 2017, and Ser. No. 14/314,743, filed on Jun. 25, 2014, both incorporated here by reference.

Having a larger field of view is useful not just for counting, but for many microscopic imaging applications. A pathologist, for example, would typically be glad to see more area of a tissue sample. The gaps due to the non-light-sensitive areas would be minor distractions in such an application.

Figure 2:
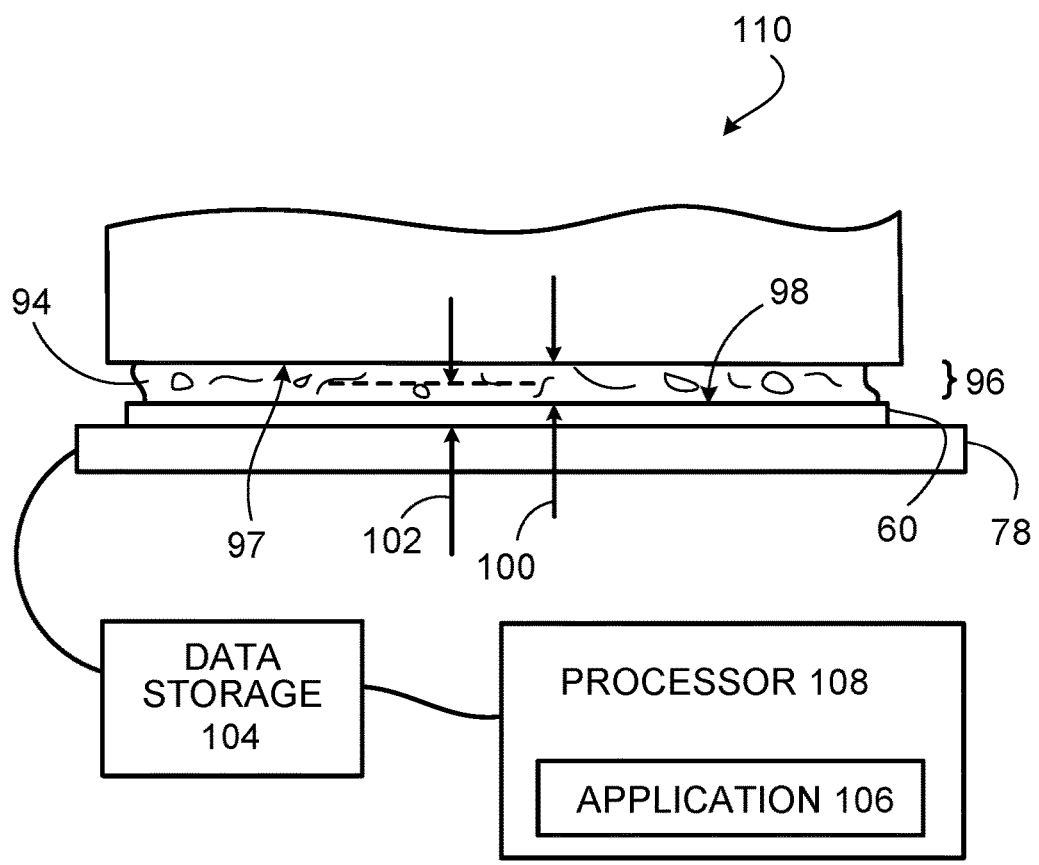
FIG. 2 is a schematic view of a blood count device.

As shown in FIG. 2 (in which the elements are not shown to scale), a large-area high-resolution high-aspect-ratio image sensor 60 can be coupled to (e.g., interconnected electrically with) a sensor drive circuit 78 that is arranged to drive the image sensor and receive image signals from the image sensor corresponding to an image of a specimen 94 held within a chamber 96. The chamber has a surface 97 that faces the light-sensitive surface 98 of the image sensor and is spaced apart from surface 98 by a precise distance 100 that is near enough to the image sensor to confine the specimen to a monolayer, with at least part of the specimen within the near field distance 102 of the image sensor. The sensor drive circuit stores the image signals from the image sensor as image data in a data storage device 104 which may be coupled to or part of the sensor drive circuit. An application 106 executed by a processor 108 coupled to the data storage device can then fetch the image data from the storage and apply image processing and analysis routines to perform a wide variety of tasks, such as blood counting, and provide the results to users or other processes. The large-area high-resolution high-aspect-ratio image sensor 60, sensor drive circuit 78, data storage device 104, processor 108, and application 106 together can comprise a blood count device 110. Additional information about lensless contact optical microscopes, their configurations, their associated devices, and their uses can be found, for example, in U.S. Pat. No. 9,041,790, issued May 6, 2015; U.S. Pat. No. 9,518,920, issued Dec. 13, 2016; and U.S. Pat. No. 9,075,225, issued Jul. 7, 2015; and in U.S. patent application Ser. No. 14/173,500, filed Feb. 5, 2014; Ser. No. 15/066,065, filed Mar. 10, 2016; all incorporated here by reference in their entirety.

Other implementations are also within the scope of the following claims.

Figure 3:
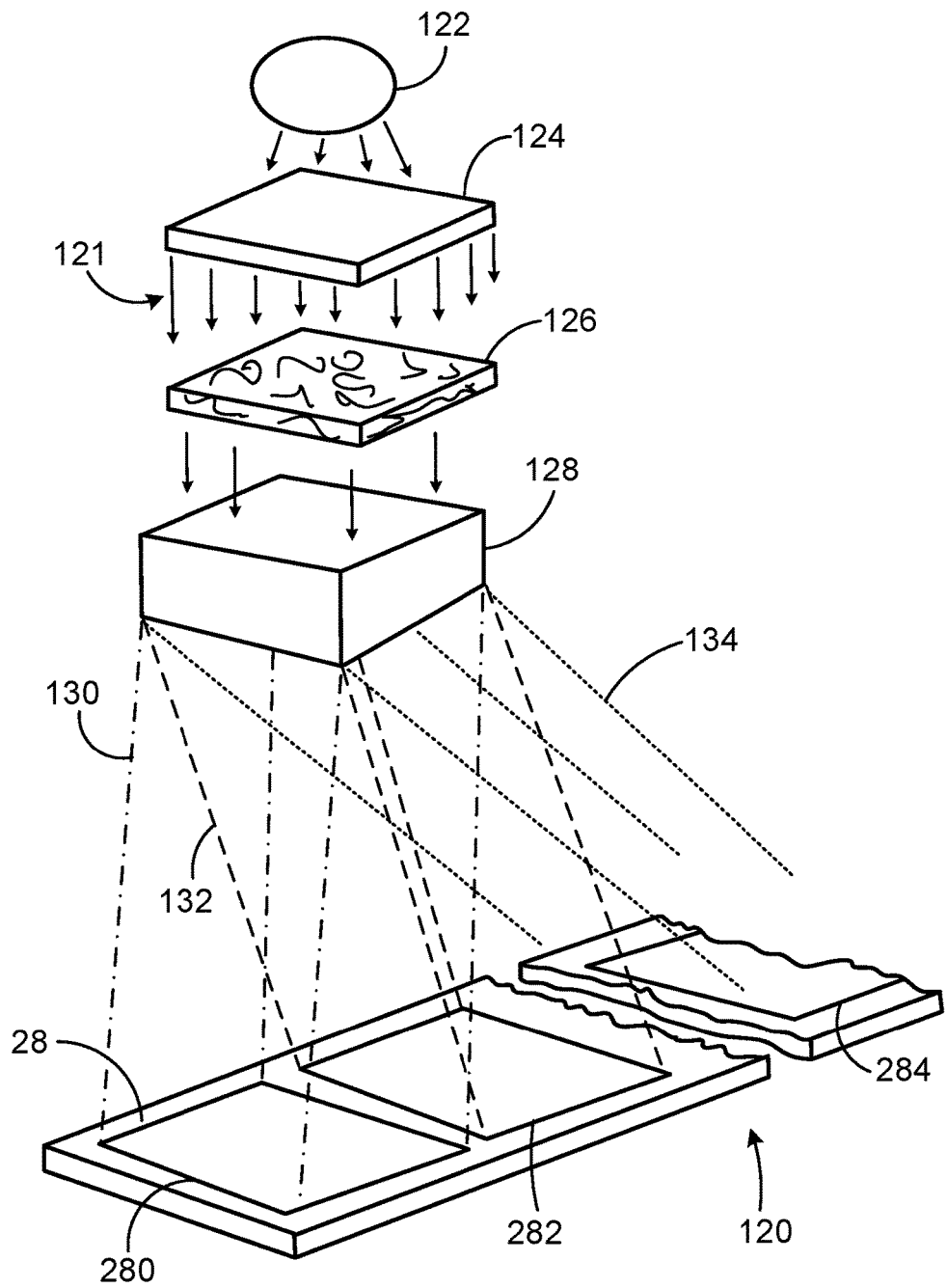
FIG. 3 is a perspective schematic view of a beam splitting arrangement.

For example, as shown in FIG. 3, high-aspect-ratio image sensors can be used in a variety of applications other than as sensors in contact optical microscopy. In some applications, such a sensor 120 could be used in lens-based microscopy or photography to receive and process different versions of an image using light 121 from a light source 122 that has passed through collimating optics 124 and a sample 126. Instead of delivering the image directly to a single low-aspect-ratio sensor for detection in a typical lens-based system, beam splitting devices 128 (such as a beam-splitting prism) could be used to split the image into two (or more) similar copies 130, 132, 134 of the image, each directed along equivalent light paths to a corresponding one of the light-sensitive subareas 280, 282, 284 of the high-aspect-ratio image sensors.

In some implementations, each of the images delivered from the beam splitting device(s) can be filtered based on wavelength (for example by using dichroic mirrors for beam splitting), permitting each of the light-sensitive subareas to be operated in a monochrome mode, without the presence of any intervening Bayer or other color filter array, to achieve highest-resolution images with multi-spectral information. In some applications, each of the images delivered from the beam splitting device can be filtered based on polarization (for example by using a polarizing beam splitter). Simultaneous multi-parametric imaging of the kind that this approach would facilitate has important applications in physiology, materials science, and other fields.

Because the light-sensitive areas all lie on a common flat surface of the sensor (the co-planarity is as good as it can be) and are separated by very precisely known distances (the relative X-Y locations of the light-sensitive areas are known precisely), in all these cases the different paths from lens or lenses to the two or more light-sensitive subareas can be arranged to have precisely the same length, and the images delivered to the different subareas can be arranged to be of exactly the same dimensions and focus.

Figure 4:
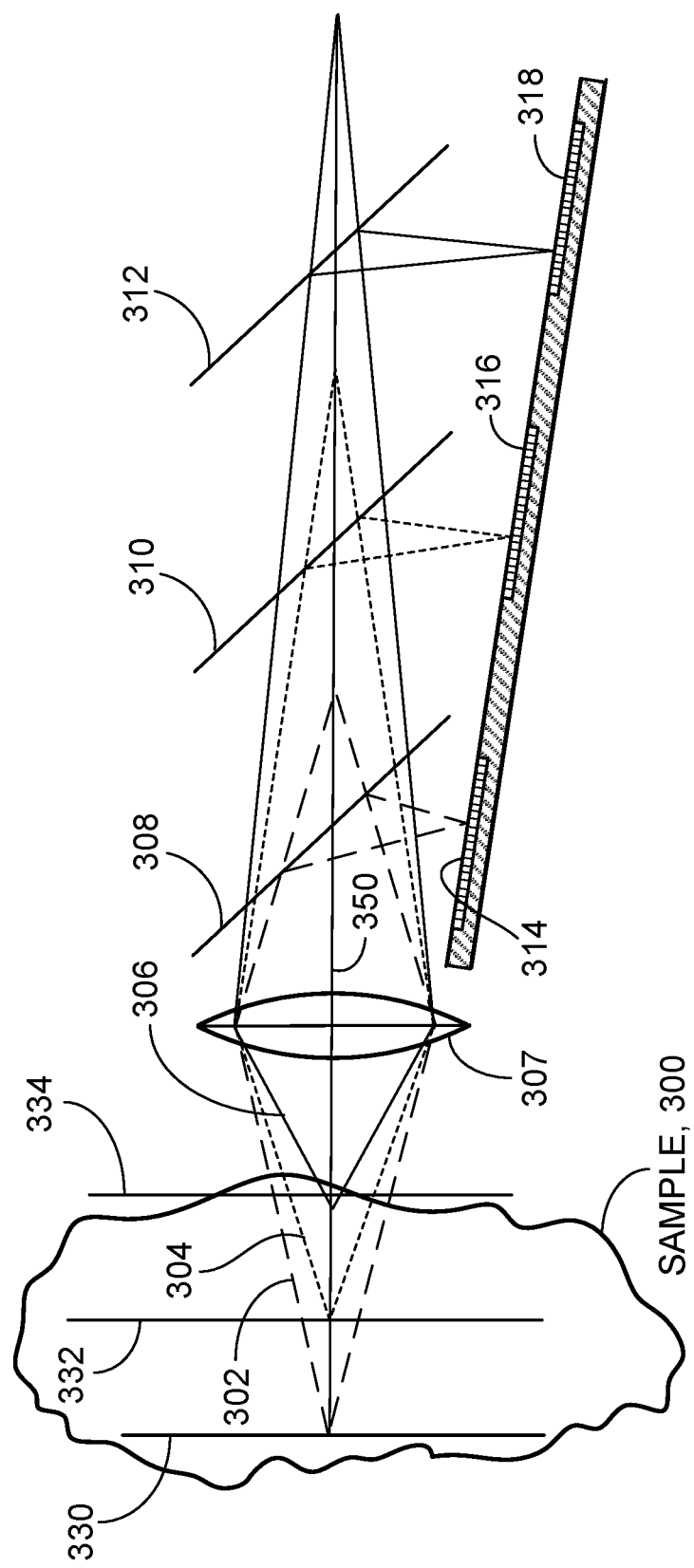
FIG. 4 is a schematic view of a beam splitting arrangement.

As shown in FIG. 4, in some applications the paths 302, 304, 306 through a lens 307 and one or more beam splitter(s) 308, 310, 312 to the light-sensitive areas can be arranged to have precisely different (rather than identical) lengths, such that the images formed on the two or more light-sensitive areas 314, 316, 318 will be aligned on the common plane of the light-sensitive areas but have different object planes 330, 332, 334 in focus, permitting simple simultaneous high-resolution multifocal imaging, amenable to further interpolation by computational means. In some cases, such as the one shown in FIG. 4, the appropriate different path lengths are achieved by tilting the strip bearing the light-sensitive areas at an angle to the optical axis 350. Other ways of achieving the appropriate different path lengths are also possible.

These conditions and scenarios described above can all be achieved by careful placement and orientation of the beam-directing optics, but without requiring efforts that would otherwise be required to align the surfaces of discrete sensors on a common plane and at a precise known separation between the subareas.

The invention claimed is:

1. An apparatus comprising
at least one component configured to provide two or more images of a sample, and
a large-area high-aspect-ratio integral image sensor having two or more light-sensitive subareas positioned to receive the two or more images from the component.

2. The apparatus of claim 1 in which the component comprises a beam-splitting component and optics to project two or more identical images of the sample onto two or more of the light-sensitive subareas.

3. The apparatus of claim 2 in which an optical path from the beam splitting component to the large-area high-aspect-ratio integral image sensor is free of any color filter pixel arrays on the image sensor.

4. The apparatus of claim 1 in which the component is configured to acquire the two or more images of the sample from two or more layers of the sample that lie at different distances from the apparatus and to focus the images on two or more of the light-sensitive subareas.

5. The apparatus of claim 1 in which the sample comprises a monolayer.

6. The apparatus of claim 1 in which the sample comprises a fluid containing elements to be counted.

7. The apparatus of claim 1 in which the sample comprises blood.

8. The apparatus of claim 1 comprising a chamber having a surface spaced from the integral image sensor surface by a predetermined distance associated with a monolayer of the sample.

9. The apparatus of claim 1 comprising a sensor drive circuit coupled to the integral image sensor.

10. The apparatus of claim 9 comprising a memory coupled to the sensor drive circuit.

11. The apparatus of claim 10 comprising a processor and an application coupled to the memory, the application being configured to perform a count of elements in the sample.

12. The apparatus of claim 1 in which the two or more light-sensitive subareas are in a row at a sensor surface, successive light-sensitive subareas along the row being separated by non-light sensitive areas.

13. The apparatus of claim 1 in which the sensor surface of the integral image sensor is flat and continuous across the two or more light-sensitive subareas.

14. The apparatus of claim 1 comprising interconnects along sides of the image sensor for making electrical contact to the light-sensitive subareas.

15. The apparatus of claim 1 comprising interconnects along a side or sides of a row or column that span two or more of the subareas for making electrical contact to the light-sensitive subareas.

16. The apparatus of claim 1 comprising interconnects along not more than the two opposite sides of a row or column that spans two or more of the subareas for making electrical contact to the light-sensitive subareas.

17. The apparatus of claim 1 comprising a processor and an application coupled to the memory, the application being configured to perform a blood count or other analysis of the sample.

18. A method comprising
receiving at two or more light-sensitive subareas of a large-area high-aspect-ratio integral image sensor two or more corresponding images of a sample, and
processing the images.

\* \* \* \* \*